United States Patent [19]

Imahori et al.

[11] 4,116,623

[45] Sep. 26, 1978

[54] CYANOTRIPHENODIOXAZINE COMPOUND

[75] Inventors: Seiichi Imahori, Kawasaki; Yukichi Murata; Sumio Suzuki, both of Yokohama, all of Japan

[73] Assignee: Mitsubishi Chemical Industries Ltd., Tokyo, Japan

[21] Appl. No.: 818,841

[22] Filed: Jul. 25, 1977

[30] Foreign Application Priority Data

Jul. 27, 1976 [JP] Japan .................................. 51-89576

[51] Int. Cl.$^2$ ...................... C09B 19/00; C07D 498/22
[52] U.S. Cl. ................................................ 8/25; 8/179; 544/75; 544/77; 544/99
[58] Field of Search .................... 544/99, 75, 77; 8/25

[56] References Cited

U.S. PATENT DOCUMENTS

| 3,635,963 | 1/1972 | Hari et al. ............................... 544/77 |
| 3,929,719 | 12/1975 | Pugin et al. ........................... 260/40 P |

*Primary Examiner*—John D. Randolph
*Attorney, Agent, or Firm*—Oblon, Fisher, Spivak, McClelland & Maier

[57] ABSTRACT

A novel cyanotriphenodioxazine compound is disclosed which is represented by the following formula:

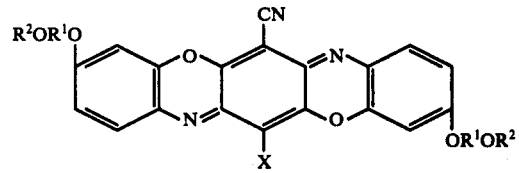

wherein X represents cyano or halogen, $R^1$ represents $C_1$-$C_4$ alkylene and $R^2$ represents $C_1$-$C_4$ alkyl, $C_1$-$C_4$ alkoxy-$C_1$-$C_4$ alkyl or $C_1$-$C_4$ alkoxy-$C_1$-$C_4$ alkoxy-$C_1$-$C_4$ alkyl and is a dyestuff suitable for dyeing synthetic fibers or cellulose acetate fibers in brilliant red shade with good fastness to light and to sublimation.

17 Claims, No Drawings

CYANOTRIPHENODIOXAZINE COMPOUND

This invention relates to a novel cyanotriphenodioxazine compound which is a useful dyestuff and a process for producing such compound.

In more particular, this invention relates to a cyanotriphenodioxazine compound represented by the following formula I:

wherein X represents cyano or halogen, $R^1$ represents $C_1$–$C_4$ alkylene and $R^2$ represents $C_1$–$C_4$ alkyl, $C_1$–$C_4$ alkoxy-$C_1$–$C_4$ alkyl or $C_1$–$C_4$ alkoxy-$C_1$–$C_4$ alkoxy-$C_1$–$C_4$ alkyl.

The compound according to this invention is produced by reacting a compound represented by the following formula II:

wherein Y represents halogen and $R^1$ and $R^2$ have the same meanings as above, with a metal cyanide in an organic medium.

This invention will be explained in detail.

The starting material of the process according to this invention is conveniently produced by cyclization of 2,5-diarylaminobenzoquinone represented by the following formula III:

wherein Z represents halogen, A represents hydrogen or —$OR^1OR^2$ and $R^1$ and $R^2$ have the same meanings as above.

In the formula I representing the compound according to this invention, the substituent X represents cyano or halogen, such as, chlorine or bromine, $R^1$ represents $C_1$–$C_4$ alkylene, such as, methylene, ethylene, trimethylene, 3-methyltrimethylene or 1-methylethylene, preferably ethylene, and $R^2$ represents $C_1$–$C_4$ alkyl, such as, methyl, ethyl, propyl or butyl, $C_1$–$C_4$ alkoxy-$C_1$–$C_4$ alkyl, such as, β-methoxyethyl, β-ethoxyethyl, β-propoxyethyl or β-butoxyethyl or $C_1$–$C_4$ alkoxy-$C_1$–$C_4$ alkoxy-$C_1$–$C_4$ alkyl, such as, β-(β'-methoxyethoxy) ethyl, β-(β'-ethoxyethoxy) ethyl, β-(β'-propoxyethoxy) ethyl or β-(β'-butoxyethoxy) ethyl.

The cyanotriphenodioxazine compound according to this invention is conveniently produced by heating a mixture of the compound represented by the formula II and a metal cyanide which are dissolved or dispersed in an organic solvent. The progress of the reaction can be observed by thin layer chromatography, and there are produced the desired products represented by the following formulae:

and/or as well as byproducts represented by the following formulae:

and wherein Y, $R^1$ and $R^2$ have the same meanings as above. In order to isolate the desired compound, thin layer column chromatography can be used.

The heating is stopped at an appropriate stage and, after the mixture is cooled, water is added to precipitate the reaction product, which is filtered off.

If necessary, an excess of metal cyanide and metal halide which is formed during the reaction are converted into a water soluble cyano complex by a known method, for example, by addition of an alkali cyanide, such as, sodium cyanide or potassium cyanide, or ammonium cyanide; alternatively, when cuprous cyanide is used, cuprous halide is oxidized with, for example, ferric chloride to a water soluble cupric halide, and then the desired product which is in the form of a precipitate is readily separated.

The organic solvent suitable for the reaction is a polar, aprotic solvent, for example, dimethylformamide, N-methylpyrrolidone, formamide, dimethylacetamide, pyridine, quinoline, acetonitrile, benzonitrile, phosphoric tris(di-methylamide), dimethyl sulfoxide or sulfolane. N-methylpyrrolidone is most preferred.

The metal cyanide is, for example, cuprous cyanide, silver cyanide, lead cyanide, potassium ferrocyanide, calcium ferrocyanide, copper ferrocyanide or zinc cyanide. Cuprous cyanide is most preferred because of its high reactivity.

The metal cyanide may be formed in situ from, for example, an alkali cyanide and a cupric salt, such as, cupric sulfate or cupric acetate.

The reaction temperature may vary over a wide range depending upon the starting material and the organic solvent employed and ranges from 20° to 250° C., preferably 130° to 210° C.

The compound represented by the formula I is a dyestuff suitable for dyeing synthetic fibers, especially polyesters such as polyethylene terephthalate, cellulose esters such as cellulose acetate, and blends or mixed fabrics thereof.

The dyestuff possesses excellent affinity to such fibers and gives dyed materials of brilliant red shade with good fastness to light.

A dyeing composition, for example, dye bath or printing paste, is prepared by dispersing at least one dyestuff represented by the formula I in an aqueous medium.

The dyeing composition may contain a dispersing agent, such as, a condensation product of a naphthalene sulfonic acid and formaldehyde, a sulfuric ester of a higher alcohol or a higher alkylbenzene sulfonate.

If desired, a carrier, such as, phenylphenols, chlorobenzenes, hydroxybenzoic esters, phenylmethylcarbinols or alkylnaphthalenes may be added to a dye bath or a printing paste.

For polyester fibers, dyeing is carried out using a dye bath having a desired dyestuff concentration at a temperature of 120° to 130° C. for 60 to 120 minutes, followed by soaping. In the case where the dye bath contains a carrier, the dyeing temperature is usually 80° to 100° C.

The dyeing of cellulose ester fibers is carried out at a temperature of 80° to 120° C. for 60 to 120 minutes.

The dyed material is of brilliant red shade and has good fastness to light and to sublimation and improved fastness to washing of resin-finished fabric.

This invention will be explained in detail by means of examples; however, it should be understood that this invention is in no way limited by these examples. In the examples "part" and "percentage" are given by weight unless otherwise specifically defined.

EXAMPLE 1

A mixture of 2g of a compound having the following structure

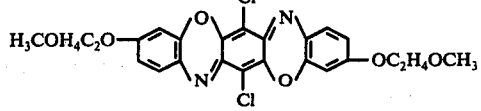

6g of cuprous cyanide and 40 ml of N-methylpyrrolidone was heated under reflux for 3 hours to effect the reaction. The reaction mass was poured into water after cooling and the precipitate was filtered out. The product was mixed with 500 ml of water containing 18g of ferric chloride and 90 ml of concentrated hydrochloric acid, and agitation was continued at 60° C. for 1 hour. After cooling and vacuum filtration, the wet cake obtained was washed with water and dried to obtain a mixture of the raw material 1-A and products represented by the following formulae 1-B, 1-C, 1-D, 1-E and 1-F:

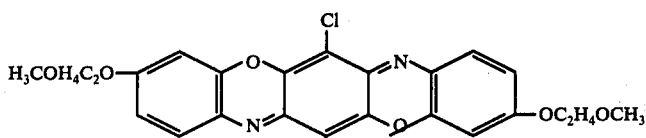

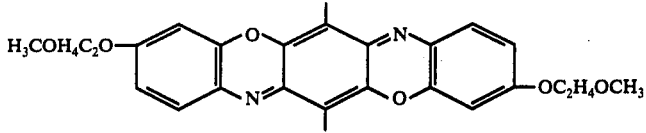

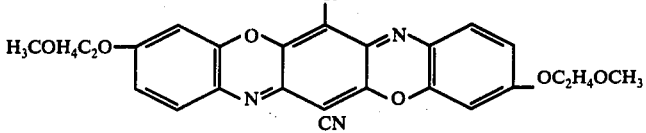

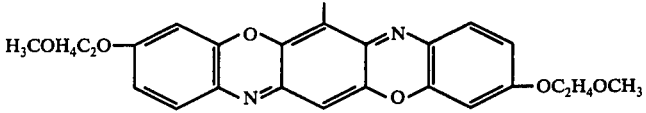

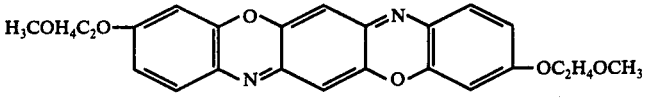

The above structures were confirmed through elementary analysis and mass spectrometry after separation of the respective components by thin layer chromatography.

The elementary analysis of the compound 1-B as $C_{25}H_{20}N_3O_6Cl$ was:

|  | C (%) | H (%) | N (%) | Cl (%) |
|---|---|---|---|---|
| Calculated | 60.79 | 4.08 | 8.51 | 7.18 |
| Found | 60.82 | 4.01 | 8.61 | 7.05 |

The molecular ion peaks measured by the mass spectrometry were:

$m/e = 493$ and 495.

The elementary analysis of the compound 1-C as $C_{26}H_{20}N_4O_6$ was:

|  | C (%) | H (%) | N (%) |
|---|---|---|---|
| Calculated | 64.46 | 4.16 | 11.56 |

|  | C (%) | H (%) | N (%) |
|---|---|---|---|
| Found | 64.31 | 4.11 | 11.45 |

The molecular ion peak of the mass spectrometry was:

m/e = 484.

The elementary analysis of the compound 1-D as $C_{24}H_{21}N_2O_6Cl$ was:

|  | C (%) | H (%) | N (%) | Cl (%) |
|---|---|---|---|---|
| Calculated | 61.48 | 4.51 | 5.97 | 7.56 |
| Found | 61.52 | 4.48 | 6.03 | 7.41 |

The molecular ion peaks of the mass spectrometry were:

m/e = 468 and 470.

The elementary analysis of the compound 1-E as $C_{25}H_{21}N_3O_6$ was:

|  | C (%) | H (%) | N (%) |
|---|---|---|---|
| Calculated | 65.35 | 4.61 | 9.15 |
| Found | 65.22 | 4.55 | 9.03 |

The molecular ion peak of the mass spectrometry was:

m/e = 459.

The elementary analysis of the compound 1-F as $C_{24}H_{22}N_2O_6$ was:

|  | C (%) | H (%) | N (%) |
|---|---|---|---|
| Calculated | 66.35 | 5.10 | 6.45 |
| Found | 66.22 | 5.04 | 6.44 |

The molecular ion peak of the mass spectrometry was:

m/e = 434.

The proportion of the compounds 1-A, 1-B, 1-C, 1-D, 1-E and 1-F in the product was approximately 5:40:20:10:20:5, by weight.

EXAMPLE 2

A mixture of 2g of a compound having the following structure

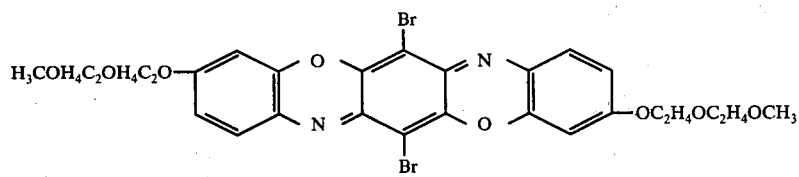

2-A 6g of cuprous cyanide and 40 ml of N-methylpyrrolidone was reacted under reflux for 1 hour. After being cooled, the reaction mass was treated by procedures similar to those of Example 1 to obtain a mixture of the raw material 2-A and compounds 2-B, 2-C, 2-D, 2-E and 2-F having the following structures:

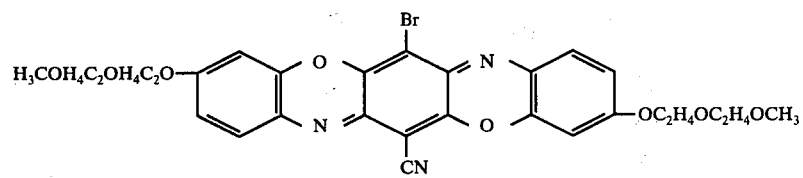

2-B

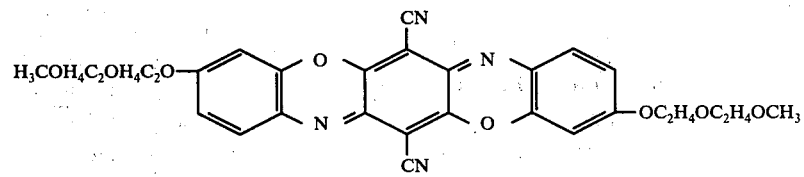

2-C

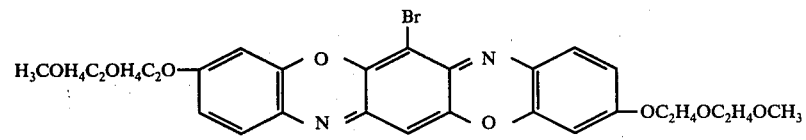

2-D

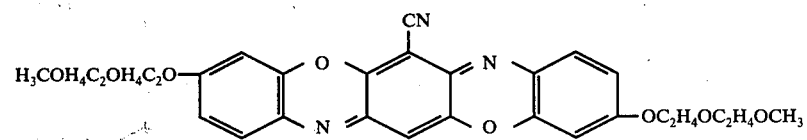

2-E and

-continued

H₃COH₄C₂OH₄C₂O—⟨benzene ring⟩—O—⟨central ring with N, N⟩—N—⟨benzene ring⟩—OC₂H₄OC₂H₄OCH₃    2-F These structures were confirmed by means of the elementary analysis and mass spectrometry after separation of the respective compounds by thin layer chromatography.

The elementary analysis of the compound 2-B as $C_{29}H_{28}N_3O_8Br$ was:

|  | C (%) | H (%) | N (%) | Br (%) |
|---|---|---|---|---|
| Calculated | 55.60 | 4.51 | 6.71 | 12.75 |
| Found | 55.71 | 4.48 | 6.78 | 12.64 |

The molecular ion peaks of the mass spectrometry were:
$m/e = 625$ and $627$.

The elementary analysis of the compound 2-C as $C_{30}H_{28}N_4O_8$ was:

|  | C (%) | H (%) | N (%) |
|---|---|---|---|
| Calculated | 62.93 | 4.93 | 9.79 |
| Found | 62.81 | 4.85 | 9.65 |

The molecular ion peak of the mass spectrometry was:
$m/e = 572$.

The elementary analysis of the compound 2-D as $C_{28}H_{29}N_2O_8Br$ was:

|  | C (%) | H (%) | N (%) | Br (%) |
|---|---|---|---|---|
| Calculated | 55.92 | 4.86 | 4.66 | 13.29 |
| Found | 55.98 | 4.81 | 4.75 | 13.15 |

The molecular ion peaks of the mass spectrometry were:
$m/e = 600$ and $602$.

The elementary analysis of the compound 2-E as $C_{29}H_{29}N_3O_8$ was:

|  | C (%) | H (%) | N (%) |
|---|---|---|---|
| Calculated | 63.61 | 5.34 | 7.67 |
| Found | 63.54 | 5.28 | 7.58 |

The molecular ion peak of the mass spectrometry was:
$m/e = 547$.

The elementary analysis of the compound 2-F as $C_{28}H_{30}N_2O_8$ was:

|  | C (%) | H (%) | N (%) |
|---|---|---|---|
| Calculated | 64.36 | 5.79 | 5.36 |
| Found | 64.22 | 5.67 | 5.28 |

The molecular ion peak of the mass spectrometry was:
$m/e = 522$.

The proportion of the compounds 2-A, 2-B, 2-C, 2-D, 2-E and 2-F in the product was approximately 5:30:40:5:15:5, by weight.

EXAMPLE 3

A mixture of 10g of a compound having following structure

H₃COH₄C₂OH₄O—⟨benzene ring⟩—O—⟨central ring with Cl, Cl, N, N⟩—N—⟨benzene ring⟩—OC₂H₄OC₂H₄OCH₃

1.5g of cuprous cyanide and 85 ml of N-methylpyrrolidone was heated under reflux for 4 hours. After being cooled, the reaction mixture was treated with procedures similar to those of Example 1 to obtain a mixture of the raw material 3-A and compounds 3-B, 3-C, 3-D, 3-E and 3-F having the following structures:

H₃COH₄C₂OH₄C₂O—⟨benzene ring⟩—O—⟨central ring with Cl, CN, N, N⟩—N—⟨benzene ring⟩—OC₂H₄OC₂H₄OCH₃

H₃COH₄C₂OH₄C₂O—⟨benzene ring⟩—O—⟨central ring with CN, CN, N, N⟩—N—⟨benzene ring⟩—OC₂H₄OC₂H₄OCH₃

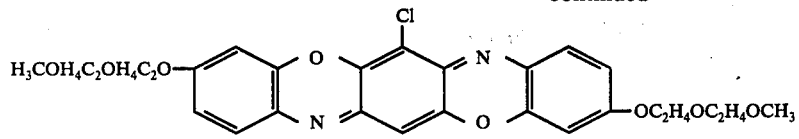

3-D

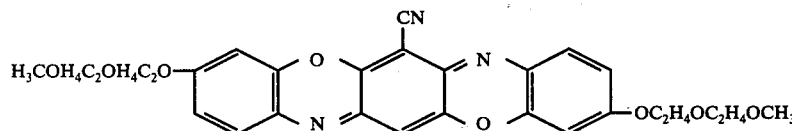

3-E and

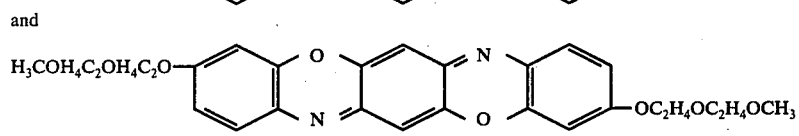

3-F

These structures were confirmed through elementary analysis and mass spectrometry after separation of the respective compounds by thin layer chromatography. The identity of the compounds 3-C, 3-E and 3-F with the compounds 2-C, 2-E and 2-F was confirmed through thin layer chromatography and infrared spectrum.

The elementary analysis of the compound 3-B as $C_{29}H_{28}N_3O_8Cl$ was:

|  | C (%) | H (%) | N (%) | Cl (%) |
|---|---|---|---|---|
| Calculated | 59.85 | 4.85 | 7.22 | 6.09 |
| Found | 59.62 | 4.78 | 7.20 | 6.21 |

The molecular ion peaks of the mass spectrometry were:
m/e = 581 and 583.

The elementary analysis of the compound 3-D as $C_{28}H_{29}N_2O_8Cl$ was:

|  | C (%) | H (%) | N (%) | Cl (%) |
|---|---|---|---|---|
| Calculated | 60.38 | 5.25 | 5.03 | 6.36 |
| Found | 60.21 | 5.22 | 5.13 | 6.45 |

The molecular ion peaks of mass spectrometry were: m/e = 556 and 558.

The proportion of the compounds 3-A, 3-B, 3-C, 3-D, 3-E and 3-F in the product was approximately 50:20:5:15:5:5, by weight.

EXAMPLE 4

A dye bath was prepared by dispersing 0.5g of the dyestuff prepared in Example 1 and containing the compounds 1-A, 1-B, 1-C, 1-D, 1-E and 1-F in 3l of water containing 1g of a condensate of naphthalene sulfonic acid-formaldehyde and 2g of sulfuric ester of a higher alcohol.

One hundred grams of polyester fiber was dyed by immersing in the bath at 130° C. for 60 minutes, followed by soaping, washing with water and drying to obtain brilliant red dyed fiber with good fastness to light and to sublimation.

The following Table shows the absorption maximum of wavelength (λ max) of each of the compounds according to this invention and shade of dyed material.

| Compound | λmax. (mμ)* | Shade** |
|---|---|---|
| 1-A | 545, 507 | Brilliant Red |
| 1-B | 562, 523 | Brilliant Bluish Red |
| 1-C | 570, 532 | Brilliant Bluish Red |
| 1-D | 540, 504 | Brilliant Yellowish Red |
| 1-E | 557, 518 | Brilliant Red |
| 1-F | 535, 499 | Brilliant Yellowish Red |
| 2-A | 550, 512 | Brilliant Red |
| 2-B | 567, 528 | Brilliant Bluish Red |
| 2-C (3-C) | 570, 532 | Brilliant Bluish Red |
| 2-D | 545, 509 | Brilliant Yellowish Red |
| 2-E (3-E) | 557, 518 | Brilliant Red |
| 2-F (3-F) | 535, 499 | Brilliant Yellowish Red |
| 3-A | 545, 507 | Brilliant Red |
| 3-B | 562, 523 | Brilliant Bluish Red |
| 3-D | 540, 504 | Brilliant Yellowish Red |

*Measured in chloroform
**Dyed according to procedures similar to those of Example 4.

What is claimed is:

1. A triphenodioxazine compound represented by the following formula:

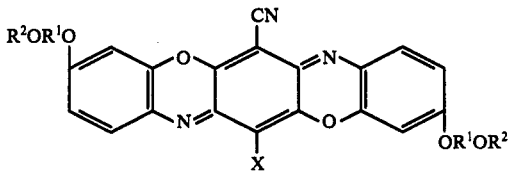

wherein X represents cyano or halogen, $R^1$ represents $C_1$–$C_4$ alkylene and $R^2$ represents $C_1$–$C_4$ alkyl, $C_1$–$C_4$ alkoxy-$C_1$–$C_4$ alkyl or $C_1$–$C_4$ alkoxy-$C_1$–$C_4$ alkoxy-$C_1$–$C_4$ alkyl.

2. A triphenodioxazine compound according to claim 1, wherein X represents cyano.

3. A triphenodioxazine compound according to claim 1, wherein X represents halogen.

4. A triphenodioxazine compound according to claim 1, wherein X represents cyano, $R^1$ represents ethylene and $R^2$ represents methyl, ethyl, propyl, butyl, β-methoxyethyl, β-ethoxyethyl, β-propoxyethyl, β-butoxyethyl, β-(β'-methoxyethoxy) ethyl, β-(β'-ethoxyethoxy) ethyl, β-(β'-propoxyethoxy) ethyl or β-(β'-butoxyethoxy) ethyl.

5. A triphenodioxazine compound according to claim 1, wherein X represents chlorine or bromine, $R^1$ represents ethylene and $R^2$ represents methyl, ethyl, propyl, butyl, β-methoxyethyl, β-ethoxyethyl, β-propoxyethyl, β-butoxyethyl, β-(β'-methoxyethoxy) ethyl, β-(β'-ethoxyethoxy)-ethyl, β-(β'-propoxyethoxy) ethyl or β-(β'-butoxyethoxy)-ethyl.

6. The triphenodioxazine compound according to claim 1 of the following structure

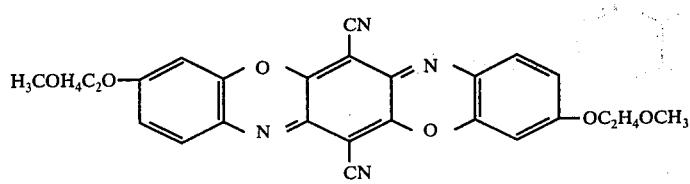

7. The triphenodioxazine compound according to claim 1 of the following structure

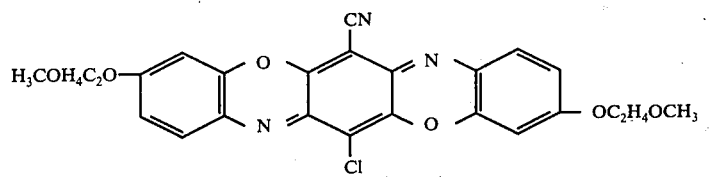

8. The triphenodioxazine compound according to claim 1 of the following structure

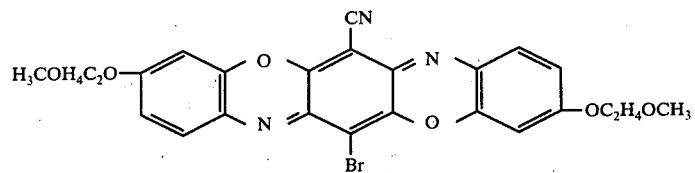

9. The triphenodioxazine compound according to claim 1 of the following structure

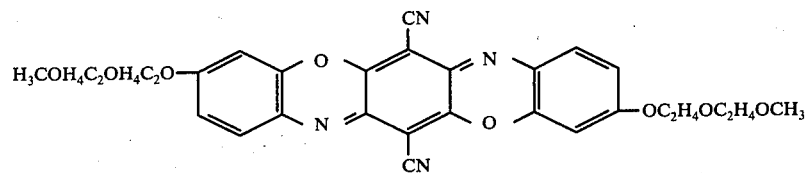

and/or

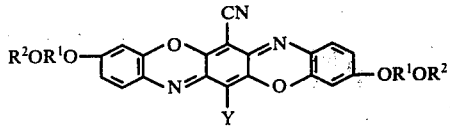

10. The triphenodioxazine compound according to claim 1 of the following structure

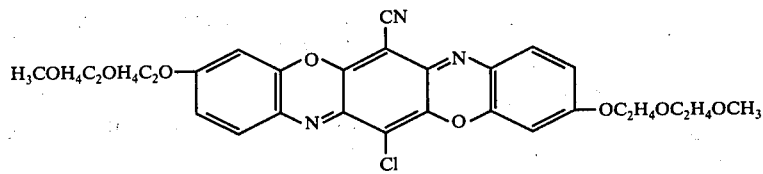

11. The triphenodioxazine compound according to claim 1 of the following structure

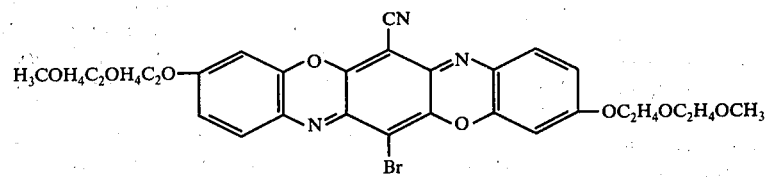

12. A process for producing a cyanotriphenodioxazine dyestuff represented by the following formulae wherein Y represents halogen, $R^1$ represents $C_1$–$C_4$ alkylene and $R^2$ represents $C_1$–$C_4$ alkyl, $C_1$–$C_4$ alkoxy- $C_1$–$C_4$ alkyl or $C_1$–$C_4$ alkoxy-$C_1$–$C_4$ alkoxy-$C_1$–$C_4$ alkyl, which comprises reacting a triphenodioxazine compound represented by the following formula:

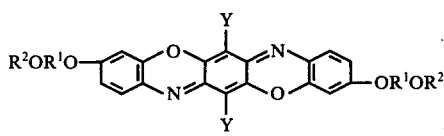

wherein Y, $R^1$ and $R^2$ have the same meanings as above, with a metal cyanide in an organic solvent.

13. A process for producing a cyanotriphenodioxazine dyestuff according to claim 12, wherein said organic solvent is a polar, aprotic solvent and the reaction is effected at a temperature of from 20° to 250° C.

14. A process for producing a cyanotriphenodioxazine dyestuff according to claim 12, wherein said metal cyanide is cuprous cyanide, silver cyanide, lead cyanide, potassium ferrocyanide, calcium ferrocyanide, copper ferrocyanide or zinc cyanide.

15. A process for producing a cyanotriphenodioxazine dyestuff according to claim 12, wherein said metal cyanide is formed in situ from an alkali cyanide and a cupric salt.

16. A dyestuff comprising compounds of the following formulae

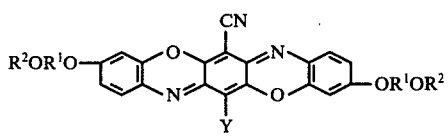

and/or

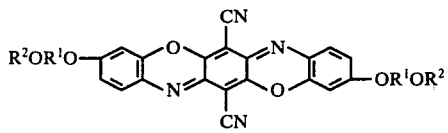

wherein Y represents halogen, $R^1$ represents $C_1$–$C_4$ alkylene and $R^2$ represents $C_1$–$C_4$ alkyl, $C_1$–$C_4$ alkoxy-$C_1$–$C_4$ alkyl or $C_1$–$C_4$ alkoxy-$C_1$–$C_4$ alkoxy-$C_1$–$C_4$ alkyl.

17. A dyestuff comprising a mixture of compounds, as coloring ingredients, of the following formulae

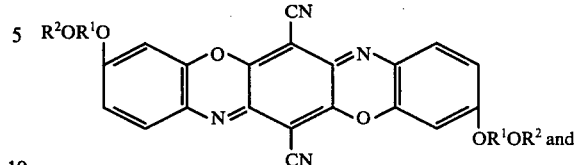

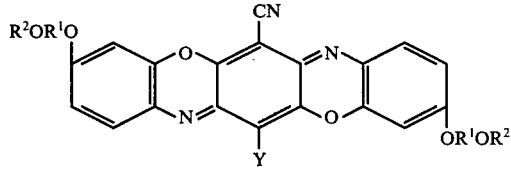

and, optionally, at least one of the compounds of the following formulae

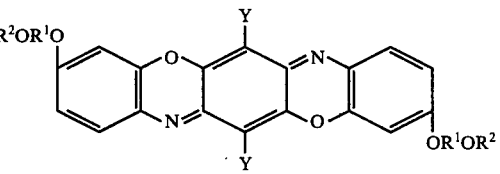

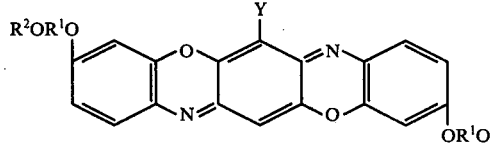

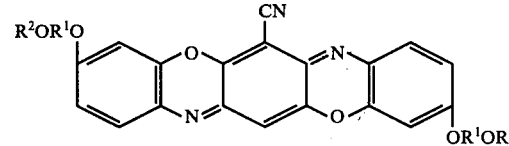

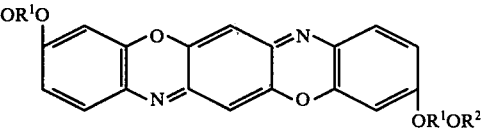

wherein Y represents halogen, $R^1$ represents $C_1$–$C_4$ alkylene and $R^2$ represents $C_1$–$C_4$ alkyl, $C_1$–$C_4$ alkoxy-$C_1$–$C_4$ alkyl or $C_1$–$C_4$ alkoxy-$C_1$–$C_4$ alkoxy-$C_1$–$C_4$ alkyl.

UNITED STATES PATENT AND TRADEMARK OFFICE
CERTIFICATE OF CORRECTION

PATENT NO. : 4,116,623

DATED : September 26, 1978

INVENTOR(S) : Seiichi Imahori et al

It is certified that error appears in the above-identified patent and that said Letters Patent are hereby corrected as shown below:

Please Correct the Priority Data to Read as Follows:

[30]  Jul. 27, 1976   Japan..............51-89576

Jul. 29, 1976   Japan..............51-90554

*Signed and Sealed this*

*Seventeenth* Day of *July 1979*

[SEAL]

*Attest:*

LUTRELLE F. PARKER

*Attesting Officer*   *Acting Commissioner of Patents and Trademarks*